United States Patent [19]

Eckhardt et al.

[11] Patent Number: 4,727,075
[45] Date of Patent: Feb. 23, 1988

[54] FUNGICIDAL 5-SUBSTITUTED PYRIMIDINE DERIVATIVES, COMPOSITIONS, AND METHOD OF USE THEREFOR

[75] Inventors: Wolfgang Eckhardt, Lörrach, Fed. Rep. of Germany; Philip Huxley, Basel, Switzerland

[73] Assignee: Ciba-Geigy Corporation, Ardsley, N.Y.

[21] Appl. No.: 897,680

[22] Filed: Aug. 18, 1986

[30] Foreign Application Priority Data

Aug. 21, 1985 [CH] Switzerland .................. 3587/85
Apr. 25, 1986 [CH] Switzerland .................. 1694/86

[51] Int. Cl.⁴ .............. A61K 31/335; A61K 31/505; C07D 239/20; C07D 317/28
[52] U.S. Cl. .................... 514/256; 544/335
[58] Field of Search .................. 544/335; 514/256

[56] References Cited
PUBLICATIONS

Japan Kokai 73 49, 776 (Chem. Abstract 79: 14655lh), (1973).

Primary Examiner—Alan L. Rotman
Assistant Examiner—J. G. Mullins
Attorney, Agent, or Firm—Edward McC. Roberts; Meredith C. Findlay

[57] ABSTRACT

The invention relates to novel pyrimidine derivatives of the general formula

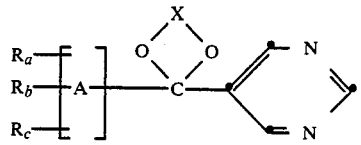

wherein
A is phenyl, phenoxyphenyl, phenylthiophenyl, biphenyl or naphthyl $R_a$, $R_b$ and $R_c$ are each independently hydrogen, halogen, cyano, nitro, $C_1$–$C_4$alkyl, $C_1$–$C_4$alkoxy, $C_1$–$C_4$haloalkyl or $C_1$–$C_4$haloalkoxy and
X is one of the following bridge elements

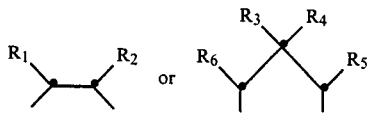

in which formulae $R_1$ and $R_2$ are each independently of the other hydrogen, $C_1$–$C_4$alkyl, $C_1$–$C_4$haloalkyl or $CH_2O$—$C_1$–$C_4$alkyl, $R_4$ is hydrogen, $C_1$–$C_4$alkyl or $CH_2OH$ and $R_3$, $R_5$ and $R_6$ are each independently hydrogen or $C_1$–$C_4$alkyl,
and to the acid addition salts thereof.

The novel compounds possess microbicidal properties and are suitable in particular for controlling phytopathogenic microorganisms.

12 Claims, No Drawings

FUNGICIDAL 5-SUBSTITUTED PYRIMIDINE DERIVATIVES, COMPOSITIONS, AND METHOD OF USE THEREFOR

The present invention relates to substituted aryldioxolanepyrimidines and aryldioxanepyrimidines of formula I below and to acid addition salts thereof. The invention further relates to the preparation of these compounds and to agrochemical compositions which contain, as active ingredient, at least one of the compounds of formula I, to the preparation of these compositions and to a method of controlling phytopathogenic microorganisms or of protecting plants from attack by said microorganisms.

Specifically the invention relates to compounds of the general formula I

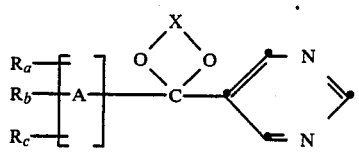

wherein

A is phenyl, phenoxyphenyl, phenylthiophenyl, biphenyl or naphthyl $R_a$, $R_b$ and $R_c$ are each independently hydrogen, halogen, cyano, nitro, $C_1$-$C_4$alkyl, $C_1$-$C_4$alkoxy, $C_1$-$C_4$haloalkyl or $C_1$-$C_4$haloalkyloxy and X is one of the following bridge elements

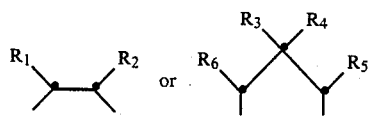

in which formulae $R_1$ and $R_2$ are each independently of the other hydrogen, $C_1$-$C_4$alkyl, $C_1$-$C_4$haloalkyl or $CH_2O$—$C_1$-$C_4$alkyl, $R_4$ is hydrogen, $C_1C_4$alkyl or $CH_2OH$ and $R_3$, $R_5$ and $R_6$ are each independently hydrogen or $C_1$-$C_4$alkyl, and to the acid addition salts thereof.

In a narrower sense, the invention relates to compounds of formula I, wherein A, $R_a$, $R_b$, $R_c$, $R_1$ and $R_2$ are as defined above and wherein $R_6$ is hydrogen and $R_3$, $R_4$ and $R_5$ are each independently hydrogen or $C_1$-$C_4$alkyl, and to the acid addition salts thereof (compound group Ia).

Depending on the number of indicated carbon atoms, alkyl by itself or as moiety of another substituent will be understood as meaning for example the following groups: methyl, ethyl, propyl, butyl and the isomers isopropyl, isobutyl, tert-butyl or sec-butyl.

Halogen by itself or as moiety of another substituent is fluorine, chlorine, bromine or iodine, with fluorine, chlorine or bromine being preferred.

The bridge elements X, together with the oxygen atoms and the common carbon atom, form dioxolane and dioxane rings.

The invention also relates to the free compounds of formula I and to their acid addition salts with organic and inorganic acids.

Examples of salt-forming acids are inorganic acids: hydrohalic acids such as hydrofluoric acid, hydrochloric acid, hydrobromic acid or hydriodic acid, as well as sulfuric acid, phosphoric acid, phosphorous acid and nitric acid; and organic acids such as acetic acid, trifluoroacetic acid, trichloroacetic acid, propionic acid, tartaric acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

At room temperatures the compounds of formula I are stable oils, resins or solids which are distinguished by very valuable microbicidal activity, in particular against fungi that attack plants. They are therefore preferably used in agriculture or related fields preventively or curatively for controlling phytopathogenic microorganisms.

Compounds of formula I which are preferred on account of their pronounced microbicidal activity are those containing the following substituents or combinations of these substituents:

for A:
  (a) phenyl, phenoxyphenyl or phenylthiophenyl; in particular
     phenyl or phenoxyphenyl;

for $R_a$, $R_b$ and $R_c$, each independently:
  (a) hydrogen, halogen, $C_1$-$C_2$alkyl, $C_1$-$_2$alkoxy, $C_1$-$C_2$haloalkyl, $C_1$-$C_2$haloalkoxy, nitro or cyano; in particular
  (b) hydrogen, halogen, $C_1$-$C_2$alkyl, $C_1$-$C_2$alkoxy, $C_1$-$C_2$haloalkoxy, nitro or cyano;

for X:

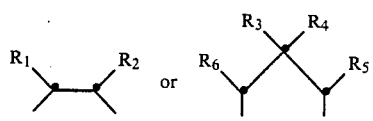

for $R_1$ and $R_2$, each independently of the other:
  (a) hydrogen, $C_1$-$C_4$alkyl, $C_1$-$C_2$haloalkyl or $CH_2O$—$C_1$-$C_2$alkyl; in particular
  (b) hydrogen, $C_1$-$C_4$alkyl or $CH_2OCH_3$;

for $R_4$:
  (a) hydrogen, $C_1$-$C_2$alkyl or $CH_2OH$; in particular
  (b) hydrogen, methyl or $CH_2OH$;

for $R_3$, $R_5$ and $R_6$, each independently:
  (a) hydrogen or $C_1$-$C_2$alkyl; in particular
  (b) hydrogen and/or methyl.

For the compound group Ia the same preferences for A, $R_a$, $R_b$ and $R_c$ apply, whereas X is preferably

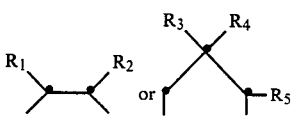

$R_1$ and $R_2$ are each independently of the other preferably
  (a) hydrogen, $C_1$-$C_4$alkyl, $C_1$-$C_2$haloalkyl or $CH_2O$—$C_1$-$C_2$alkyl; in particular
  (b) hydrogen, $C_1$-$C_4$alkyl or $CH_2OCH_3$; and $R_3$, $R_4$ and $R_5$ are each independently preferably hydrogen or $C_1$-$C_2$alkyl.

Within the scope of the substituent combinations recited above, particularly preferred compounds of formula I or of compound group Ia are those which contain the following substituents or substituent combinations:

for A: phenyl or phenoxyphenyl;
for $R_a$, $R_b$ and $R_c$, each independently: chlorine or methyl, in particular in the 2- and/or 4-positions;
for X:

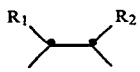

for $R_1$: $C_1$–$C_3$alkyl or $CH_2OCH_3$;
for $R_2$: hydrogen.

Compounds of formula I are also preferred wherein A in combination with $R_a$, $R_b$ and $R_c$ is 2,4-dichlorophenyl, 2-fluoro-4-chlorophenyl, 2-cyano-4-chlorophenyl, 2-methyl-4-chlorophenyl, p-chlorophenoxy, 2-methyl-4-(p-chlorophenoxy) or 2-chloro-4-(p-chlorophenoxy), and $R_1$ to $R_6$ are hydrogen or $C_1$–$C_4$alkyl, $R_1$ to $R_6$ together containing not more than 5 carbon atoms.

The compounds of formula I can be prepared as follows:

Method A

In a ketalisation reaction, a ketone of formula II

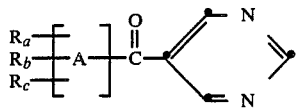

is reacted with a diol of formula III

HO—X—OH       (III)

in which formulae A, $R_a$, $R_b$, $R_c$ and X are as defined for formula I, in an inert solvent and in the absence or presence of an acid.

Method B

A ketone of formula IV

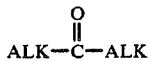

is reacted with a diol of formula III, in an inert solvent and in the absence or presence of an acid, to give a compound of formula V

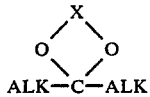

in which formulae ALK is $C_1$–$C_4$alkyl and X is as defined for formula I, and directly afterwards, without isolating the resultant compound of formula V, ketalising a ketone of formula II with said compound of formula V, in the presence of an acid.

These reactions may be carried out by procedures analogous to known ketalisation reactions, for example by procedures analogous to the preparation of 2-bromomethyl-2,4-diphenyl-1,3-dioxolane [Synthesis, 1974 (I), 23].

In a preferred embodiment of the ketalisation, both reaction partners are heated under reflux for several hours together with an entrainer, in one of the customary solvents. Examples of suitable entrainers are benzene, toluene, xylene, chloroform or carbon tetrachloride. The addition of a strong acid, e.g. p.toluenesulfonic acid, may be used with advantage to accelerate the reaction. In this case, suitable organic solvents are e.g. aromatic hydrocarbons such as benzene, toluene, xylene etc. and saturated hydrocarbons such as n-hexane. Inorganic or organic acids may also be used as reaction accelerators. Examples of inorganic acids are hydrochloric acid, hydrobromic acid, hydriodic acid, sulfuric acid, phosphoric acid, phosphorous acid and nitric acid. Examples of organic acids are acetic acid, trichloroacetic acid, oxalic acid, benzenesulfonic acid, methanesulfonic acid and p-toluenesulfonic acid.

The reaction temperatures of the ketalisation reactions are in the range from 20° to 180° C., preferably from 40° to 150° C.

The described processes constitute an object of the present invention.

In the above-described ketalisation reactions of ketones with substituted $\alpha,\beta$- or $\alpha,\gamma$-diols there are formed mixtures of diastereoisomers of the resulting ketals provided at least one of the substituents $R_1$ to $R_6$ has a meaning other than hydrogen. Accordingly, in general mixtures of diastereoisomers of the final product of formula I are formed from the starting ketones.

The separation of the two diastereoisomers and enantiomers may be effected in conventional manner. The two isomers may exhibit different microbicidal activity. In general, the mixtures of diastereoisomers are employed for practical purposes.

The invention relates to all isomeric compounds of formula I and to their salts.

The following individual compounds, either as individual isomers A or B or as a mixture of isomers (A,B), are preferred on account of their biological activity:

5-[2-(2',4'-dichlorophenyl)-4-ethyl-1,3-dioxolan-2yl]-pyrimidine [comp. 1.3a,b; 1.3a; 1.3b]

5-[2-(2',4'-dichlorophenyl)-4-propyl-1,3-dioxolan-2-yl]pyrimidine [comp. 1.4a; 1.4b; 1.4a,b]

5-[2-(2',4'-dichlorophenyl)-4-methoxymethyl-1,3-dioxolan-2yl]pyrimidine [comp. 1.7a; 1.7b; 1.7a,b]

5-[2-(2',4'-dichlorophenyl)-5-ethyl-5-methyl-1,3-dioxan-2yl]pyrimidine [comp. 2.19a,b; especially 2.19a]

5-[2-(2',4'-dichlorophenyl)-4-methyl-1,3-dioxan-2yl]-pyrimidine [comp. 3.6a,b]

5-[2-(2',4'-dichlorophenyl)-4,5-dimethyl-1,3-dioxolan-2yl]pyrimidine [comp. 1.6a; 1.6b; 1.6a,b]

5-[2-(2',4'-dichlorophenyl)-5,5-dimethyl-1,3-dioxan-2yl]pyrimidine [comp. 2.2]

5-[2-(2',4'-dichlorophenyl)-4,6-dimethyl-1,3-dioxan-2yl]pyrimidine [comp. 3.1]

5-[2-(2',4'-dichlorophenyl)-4,5,6-trimethyl-1,3-dioxan-2yl]pyrimidine comp. [3.2]

5-[2-(2'-cyano-4'-chlorophenyl)-5-ethyl-5-methyl-1,3-dioxan-2yl]pyrimidine [comp. 2.23a,b]

5-[2-(2',4'-dichlorophenyl)-4-ethyl-1,3-dioxan-2yl]-pyrimidine [comp. 3,11a,b]

5-[2-(2'-chloro-4'-p-chlorophenoxyphenyl)-4-ethyl-1,3-dioxan-2yl]pyrimidine [comp. 2.25a,b].

Some of the starting materials of formula II employed for the preparation of the final products of formula I are novel and constitute an object of the present invention. They can be prepared by methods known per se, e.g. by reaction of carboxylates of the formula

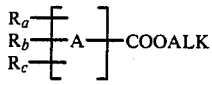

with halopyrimidines of the formula

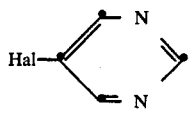

in which formulae ALK is $C_1$-$C_4$alkyl, preferably methyl or ethyl, and Hal is halogen, preferably chlorine or bromine, and A, $R_a$, $R_b$ and $R_c$ are as defined for formula I, in an inert organic solvent, in the presence of n-butyl lithium and in the temperature range from $-150°$ to $25°$ C.

The following compound

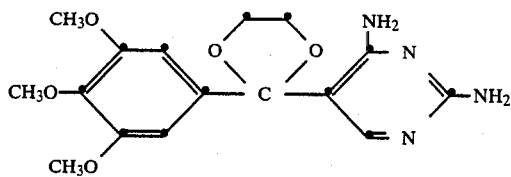

is described in the literature as an aryldioxolanepyrimidine derivative (q.v. e.g. Japanese Kokai 73 49,776). This structure type is known as potentiator for sulfonamides for controlling infectious diseases in mammals.

Surprisingly, it has been found that the compounds of formula I of this invention have, for practical field application purposes, a very advantageous microbicidal spectrum against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Fungi imperfecti (e.g. Botrytis, Helminthosporium, Fusarium, Septoria, Cercospora, Pyricularia, Alternaria); Basidiomycetes (e.g. the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings aginst fungus infections as well as against phytopathogenic fungi which occur in the soil.

The compounds of this invention are particularly well tolerated by plants.

Accordingly, the invention also relates to microbicidal compositions as well as to the use of the compounds of formula I for controlling phytopathogenic microorganisms, in particular phytopathogenic fungi, or for protecting plants from attack by said microorganisms.

The invention further embraces the preparation of agrochemical compositions, which comprises homogeneously mixing the active ingredient with one or more compounds or groups of compounds described herein.

The invention furthermore relates to a method of treating plants, which comprises applying thereto the compounds of formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This recitation constitutes no limitation.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl glycerol, lysolecithin, plasmalogenes or cardiolipin, which can be obtained e.g. from animal or plant cells, in particular from the brain, heart, liver, egg yokes or soybeans. Examples of useful physical forms are phosphatidyl choline mixtures. Examples of synthetic phospholipids are dioctanoylphosphatidyl choline and dipalmitoylphosphatidyl choline.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene, oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions constitute an object of the present invention.

The invention is illustrated in more detail by the following non-limitative Examples.

1. PREPARATORY EXAMPLES

Example 1.1: Preparation of

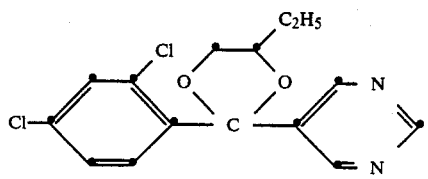

5-[2-(2',4'-Dichlorophenyl)-4-ethyl-1,3-dioxolan-2-yl]pyrimidine

In a water separator, 41.6 g (0.4 mole) of acetone dimethyl acetal and 36 g (0.4 mole) of 1,2-butanediol and a trace of p-toluenesulfonic acid are stirred under reflux for 2 hours in 300 ml of 1,1,1-trichloroethane. After cooling, 10.1 g (0.04 mole) of 5-(2,4-dichlorophenyl)ketopyrimidine and 15.2 g (0.08 mole) of p-toluenesulfonic acid are added, and the reaction mixture is stirred for 24 hours in a water separator at boiling temperature. Then a further 7.2 g (0.08 mole) of 1,2-butanediol and 4 drops of concentrated sulfuric acid are added, and the mixture is stirred overnight under reflux. Subsequently, another 7.2 g (0.08 mole) of 1,2-butanediol and 4 drops of concentrated sulfuric acid are added, and the mixture is stirred overnight under reflux. Subsequently, another 7.2 g (0.08 mole) of 1,2-butanediol and 4 drops of concentrated sulfuric acid are added, and the mixture is stirred for a further 16 hours at boiling temperature in a water separator. After cooling, the reaction mixture is extracted, in succession, three times with 1N sodium hydroxide solution and once with water, the organic phase is dried over sodium sulfate and filtered, and the filtrate is concentrated. The crude product is purified through a flash column packed with silica gel (eluant: a 3:1 mixture of petroleum ether and ethyl acetate), affording 0.6 g of an isomer A ($n_D^{40}$ 1.5528) and 0.35 g of an isomer B ($n_D^{40}$ 1.5634) as well as 1.5 g of a mixture of isomers ($n_D^{40}$ 1.5654).

Example 1.2: Preparation of

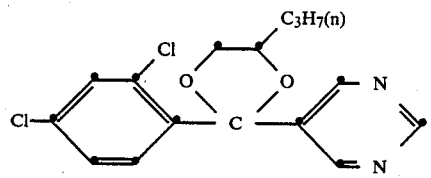

5-[2'-4'-Dichlorophenyl)-4-n-propyl-1,3-dioxolan-2-yl]pyrimidine 8.9 g (0.035 mole) of 5-(2,4-dichlorobenzoyl)pyrimidine, 5.5 g (0.0525 mole) of 1,2-pentanediol, 14 g (0.0735 mole) of p-toluenesulfonic acid and 35 ml of n-butanol in 300 ml of toluene are stirred for 20 hours at boiling temperature (bath temperature 160° C.) in a three-necked flask fitted with a Soxhlet condenser and filled with 100 g of molecular sieve (0.5 mm). After the reaction mixture has cooled to room temperature, it is extracted three times with water, the organic phase is then dried over sodium sulfate and filtered, and the filtrate is concentrated in a water-jet vacuum. The crude product is purified through a flash column packed with silica gel (eluant: a 1:3 mixture of ethyl acetate and petroleum ether). 3.1 g of an isomer A ($n_D^{40}$ 1.5522), 3.4 g of an isomer B ($n_D^{40}$ 1.5578) and 0.6 g of a mixture of isomers A/B ($n_D^{40}$ 1.5551) are thereby isolated. The total yield is 7.1 g (60% of theory).

Example 1.3: Preparation of

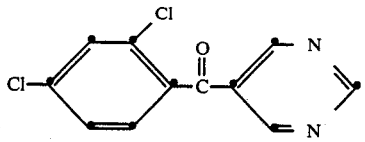

5-(2',4'-dichlorobenzoyl)pyrimidine 61.8 g (0.3 mole) of methyl 2,4-dichlorobenzoate and 52.2 g (0.33 mole) of 5-bromopyrimidine are dissolved in a mixture of 400 ml of tetrahydrofuran and 200 ml of diethyl ether. After the addition of 30 g of molecular sieve, the reaction mixture is stirred for ½ hour at room temperature and then cooled to about −120° C. 187.2 ml (0.3 mole) of butyl lithium as a 1.6 molar solution in hexane are added dropwise at this temperature. The reaction mixture is then stirred for 1½ hours in the temperature range from −100° to −130° C. Subsequently, while allowing the temperature to increase to room temperature, stirring is continued until the reaction is complete. 300 ml of 10% ammonium chloride solution are then added dropwise, and the reaction mixture is extracted three times with ethyl acetate. The organic solution is dried over sodium sulfate and then filtered, and the filtrate is concentrated. The resultant crude product is then purified through a flash column packed with silica gel (eluant: a 3:1 mixture of petroleum ether and ethyl acetate), affording 45 g (59.3% of theory) of the title compound with a melting point of 75°–78° C.

By following procedures analogous to those in Eamples 1.1 and 1.2 described above, the compounds of the present invention listed below can be prepared as—unless otherwise specifically stated—mixtures of diastereoisomers in different ratios. The resultant isomers A, B and C are characterised by physical data. No inferences concerning the absolute configuration of these isomers can be drawn from said data.

(In the Tables Ph is

)

TABLE 1

Compounds of the formula

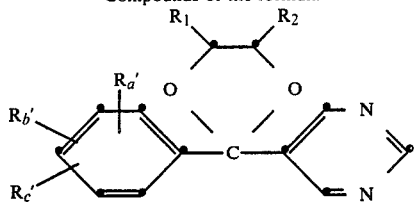

| Comp. | $R_a'$ | $R_b'$ | $R_c'$ | $R_1$ | $R_2$ | Physical data |
|---|---|---|---|---|---|---|
| 1.1 | 2-Cl | 4-Cl | H | H | H | $n_D^{40}$ 1.5798 |
| 1.2 | 2-Cl | 4-Cl | H | CH$_3$ | H | $n_D^{40}$ 1.5722 |
| 1.3a | 2-Cl | 4-Cl | H | C$_2$H$_5$ | H | $n_D^{40}$ 1.5528 (isomer A) |
| 1.3b | 2-Cl | 4-Cl | H | C$_2$H$_5$ | H | $n_D^{40}$ 1.5634 (isomer B) |
| 1.3a,b | 2-Cl | 4-Cl | H | C$_2$H$_5$ | H | $n_D^{40}$ 1.5654 (isomers A + B) |
| 1.4a | 2-Cl | 4-Cl | H | C$_3$H$_7$(n) | H | $n_D^{40}$ 1.5522 (isomer A) |
| 1.4b | 2-Cl | 4-Cl | H | C$_3$H$_7$(n) | H | $n_D^{40}$ 1.5578 (isomer B) |
| 1.4a,b | 2-Cl | 4-Cl | H | C$_3$H$_7$(n) | H | $n_D^{40}$ 1.5557 (isomers A + B) |
| 1.5 | 2-Cl | 4-Cl | H | C$_4$H$_9$(n) | H | $n_D^{40}$ 1.5492 |
| 1.6a | 2-Cl | 4-Cl | H | CH$_3$ | CH$_3$ | m.p. 92–96° C. (isomer A) |
| 1.6b | 2-Cl | 4-Cl | H | CH$_3$ | CH$_3$ | m.p. 88–92° C. (isomer B) |
| 1.6c | 2-Cl | 4-Cl | H | CH$_3$ | CH$_3$ | m.p. 85–87° C. (isomer C) |
| 1.6a,b | 2-Cl | 4-Cl | H | CH$_3$ | CH$_3$ | m.p. 96–101° C. (isomers A + B) |
| 1.7a | 2-Cl | 4-Cl | H | CH$_2$OCH$_3$ | H | $n_D^{40}$ 1.5619 (isomer A) |
| 1.7b | 2-Cl | 4-Cl | H | CH$_2$OCH$_3$ | H | $n_D^{40}$ 1.5552 (isomer B) |
| 1.7a,b | 2-Cl | 4-Cl | H | CH$_2$OCH$_3$ | H | $n_D^{40}$ 1.5615 (isomers A + B) |
| 1.8a | 2-Cl | 4-Cl | H | CH$_2$Cl | H | $n_D^{50}$ 1.5763 (isomer A) |
| 1.8b | 2-Cl | 4-Cl | H | CH$_2$Cl | H | $n_D^{50}$ 1.5783 (isomer B) |
| 1.8a,b | 2-Cl | 4-Cl | H | CH$_2$Cl | H | $n_D^{50}$ 1.5746 (isomers A + B) |
| 1.9 | 2-Cl | 4-Br | H | H | H | |
| 1.10 | 2-Cl | 4-Br | H | CH$_3$ | H | |
| 1.11a | 2-Cl | 4-Br | H | C$_2$H$_5$ | H | $n_D^{50}$ 1.5510 (isomer A) |
| 1.11b | 2-Cl | 4-Br | H | C$_2$H$_5$ | H | $n_D^{50}$ 1.5641 (isomer B) |
| 1.11a,b | 2-Cl | 4-Br | H | C$_2$H$_5$ | H | $n_D^{50}$ 1.5481 (isomers A + B) |
| 1.12 | 2-Cl | 4-Br | H | C$_3$H$_7$(n) | H | $n_D^{50}$ 1.5408 |
| 1.13 | 2-Cl | 4-Br | H | CH$_3$ | CH$_3$ | m.p. 108–111° C. |
| 1.14 | 2-Cl | 4-Br | H | CH$_2$OCH$_3$ | H | $n_D^{50}$ 1.5638 |
| 1.15 | 2-Cl | 4-Br | H | CH$_2$Cl | H | $n_D^{50}$ 1.5767 |
| 1.16 | 2-Cl | 4-F | H | H | H | $n^{50}$ 1.5691 |
| 1.17 | 2-Cl | 4-F | H | CH$_3$ | H | |
| 1.18 | 2-Cl | 4-F | H | C$_2$H$_5$ | H | $n_D^{50}$ 1.5610 |
| 1.19 | 2-Cl | 4-F | H | C$_3$H$_7$(n) | H | $n_D^{50}$ 1.5573 |
| 1.20 | 2-OCHF$_2$ | 4-Cl | H | CH$_3$ | H | |
| 1.21 | 2-OCHF$_2$ | 4-Cl | H | C$_2$H$_5$ | H | |
| 1.22 | 2-OCHF$_2$ | 4-Cl | H | C$_3$H$_7$(n) | H | viscous |
| 1.23 | 2-OCF$_3$ | 4-Cl | H | C$_2$H$_5$ | H | |
| 1.24 | 2-OCF$_3$ | 4-Cl | H | C$_3$H$_7$(n) | H | viscous |
| 1.25 | 2-NO$_2$ | 4-NO$_2$ | H | C$_2$H$_5$ | H | |
| 1.26 | 2-NO$_2$ | 4-NO$_2$ | H | C$_3$H$_7$(n) | H | |
| 1.27 | H | 4-Cl | H | C$_3$H$_7$(n) | H | |
| 1.28 | 3-Cl | 4-Cl | H | C$_3$H$_7$(n) | H | |
| 1.29 | 2-CH$_3$ | 4-Cl | H | C$_2$H$_5$ | H | |
| 1.30 | 2-Cl | 4-Cl | 6-Cl | C$_2$H$_5$ | H | |
| 1.31 | 2-OCH$_3$ | 4-Cl | H | C$_3$H$_7$(n) | H | |
| 1.32 | 2-CN | 4-Cl | H | C$_3$H$_7$(n) | H | |
| 1.33 | 4-O—Ph—Cl(4) | H | H | H | H | |
| 1.34 | 4-O—Ph—Cl(4) | H | H | CH$_3$ | CH$_3$ | m.p. 122–125° C. |
| 1.35 | 4-O—Ph—Cl(4) | H | H | CH$_3$ | H | |
| 1.36 | 4-O—Ph—Cl(4) | H | H | C$_2$H$_5$ | H | $n_D^{50}$ 1.5826 |
| 1.37 | 4-O—Ph—Cl(4) | H | H | C$_3$H$_7$(n) | H | $n_D^{50}$ 1.5793 |
| 1.38 | 4-O—Ph—Cl(4) | 2-Cl | H | C$_2$H$_5$ | H | |
| 1.39 | 4-O—Ph—Cl(4) | 2-Cl | H | CH$_3$ | H | |
| 1.40 | 4-O—Ph—Cl(4) | 2-Cl | H | C$_3$H$_7$(n) | H | $n_D^{50}$ 1.5613 |
| 1.41 | 4-O—Ph—Cl(4) | 2-CH$_3$ | H | CH$_3$ | H | |
| 1.42 | 4-O—Ph—Cl(4) | 2-CH$_3$ | H | C$_2$H$_5$ | H | $n_D^{50}$ 1.5664 |
| 1.43 | 4-O—Ph—Cl(4) | 2-CH$_3$ | H | C$_3$H$_7$(n) | H | |
| 1.44 | 4-O—Ph—Cl(4) | 2-CH$_3$ | H | CH$_2$OCH$_3$ | H | $n_D^{50}$ 1.5784 |
| 1.45 | 4-O—Ph—Cl(4) | 2-Cl | H | CH$_2$OCH$_3$ | H | $n_D^{50}$ 1.5743 |
| 1.46 | 4-O—Ph—Br(4) | H | H | C$_2$H$_5$ | H | |
| 1.47 | 4-O—Ph—Br(4) | 2-Cl | H | C$_2$H$_5$ | H | |
| 1.48 | 4-O—Ph—Br(4) | 2-Cl | H | CH$_3$ | H | $n_D^{50}$ 1.5850 |
| 1.49 | 4-O—Ph—Br(4) | 2-Cl | H | C$_3$H$_7$(n) | H | |
| 1.50 | 4-O—Ph—Br(4) | 2-CH$_3$ | H | C$_2$H$_5$ | H | |
| 1.51 | 4-O—Ph—Br(4) | 2-CH$_3$ | H | CH$_3$ | H | |
| 1.52 | 4-S—Ph—Cl(4) | H | H | CH$_3$ | H | |
| 1.53 | 4-S—Ph—Cl(4) | H | H | C$_2$H$_5$ | H | |
| 1.54 | 4-S—Ph—Cl(4) | 2-Cl | H | CH$_3$ | H | dark oil |
| 1.55 | 4-S—Ph—Cl(4) | 2-Cl | H | C$_2$H$_5$ | H | |
| 1.56 | 4-S—Ph—Cl(4) | 2-CH$_3$ | H | CH$_3$ | H | |

TABLE 1-continued

Compounds of the formula

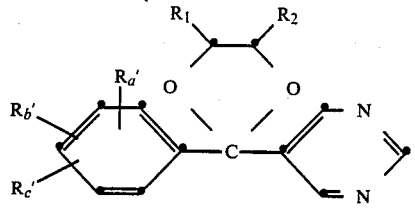

| Comp. | $R_a'$ | $R_b'$ | $R_c'$ | $R_1$ | $R_2$ | Physical data |
|---|---|---|---|---|---|---|
| 1.57 | 4-S—Ph—Cl(4) | 2-CH$_3$ | H | C$_2$H$_5$ | H | viscous |
| 1.58 | 4-Ph | H | H | C$_2$H$_5$ | H | $n_D^{40}$ 1.5733 |
| 1.59 | 4-OCH$_3$ | | H | C$_2$H$_5$ | H | |
| 1.60 | 2-F | 4-Cl | H | H | H | |
| 1.61 | 2-F | 4-Cl | H | CH$_3$ | H | |
| 1.62a | 2-F | 4-Cl | H | CH$_3$ | CH$_3$ | $n_D^{50}$ 1.5352 (isomer A) |
| 1.62b | 2-F | 4-Cl | H | CH$_3$ | CH$_3$ | $n_D^{50}$ 1.5338 (isomer B) |
| 1.62a,b | 2-F | 4-Cl | H | CH$_3$ | CH$_3$ | $n_D^{50}$ 1.5304 (isomers A + B) |
| 1.63a | 2-F | 4-Cl | H | C$_2$H$_5$ | H | $n_D^{50}$ 1.5331 (isomer A) |
| 1.63b | 2-F | 4-Cl | H | C$_2$H$_5$ | H | $n_D^{50}$ 1.5350 (isomer B) |
| 1.63a,b | 2-F | 4-Cl | H | C$_2$H$_5$ | H | $n_D^{50}$ 1.5505 (isomers A + B) |
| 1.64a | 2-F | 4-Cl | H | C$_3$H$_7$(n) | H | $n_D^{50}$ 1.5269 (isomer A) |
| 1.64b | 2-F | 4-Cl | H | C$_3$H$_7$(n) | H | $n_D^{50}$ 1.5291 (isomer B) |
| 1.64a,b | 2-F | 4-Cl | H | C$_3$H$_7$(n) | H | $n_D^{50}$ 1.5293 (isomers A + B) |
| 1.65 | 2-F | 4-Cl | H | CH$_2$OCH$_3$ | H | |
| 1.66 | H | 4-Cl | H | H | H | $n_D^{40}$ 1.5823 |

TABLE 2

Compounds of the formula

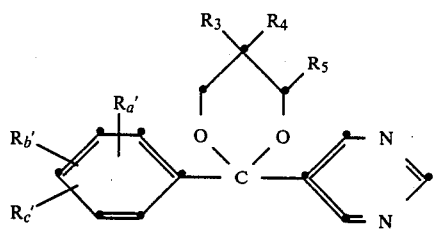

| Comp. | $R_a'$ | $R_b'$ | $R_c'$ | $R_3$ | $R_4$ | $R_5$ | Physical data |
|---|---|---|---|---|---|---|---|
| 2.1 | 2-Cl | 4-Cl | H | H | H | H | m.p. 99–102° C. |
| 2.2 | 2-Cl | 4-Cl | H | CH$_3$ | CH$_3$ | H | m.p. 108–111° C. |
| 2.3 | 2-Cl | 4-Cl | H | CH$_3$ | CH$_3$ | CH$_3$ | $n_D^{50}$ 1.5486 |
| 2.4 | 2-Cl | 4-Cl | 6-Cl | CH$_3$ | CH$_3$ | H | m.p. 123–125° C. |
| 2.5 | 2-Cl | 4-Br | H | CH$_3$ | CH$_3$ | H | |
| 2.6 | 2-Cl | 4-F | H | CH$_3$ | CH$_3$ | H | |
| 2.7 | 4-O—Ph—Cl(4) | H | H | CH$_3$ | CH$_3$ | H | m.p. 63–66° C. |
| 2.8 | 4-O—Ph—Cl(4) | 2-Cl | H | CH$_3$ | CH$_3$ | H | |
| 2.9 | 4-O—Ph—Cl(4) | 2-CH$_3$ | H | CH$_3$ | CH$_3$ | H | m.p. 68–71° C. |
| 2.10 | 4-O—Ph—(4) | 2-Cl | H | CH$_3$ | CH$_3$ | H | |
| 2.11 | 4-O—Ph—Br(4) | 2-CH$_3$ | H | CH$_3$ | CH$_3$ | H | |
| 2.12 | 4-Ph | H | H | CH$_3$ | CH$_3$ | H | m.p. 183–185° C. |
| 2.13 | 4-S—Ph—Cl(4) | H | H | H | H | H | |
| 2.14 | 4-S—Ph—Cl(4) | 2-Cl | H | CH$_3$ | CH$_3$ | H | viscous |
| 2.15 | 4-S—Ph—Cl(4) | 2-CH$_3$ | H | CH$_3$ | CH$_3$ | H | oil |
| 2.16 | 4-O—Ph—Cl(4) | 2-CH$_3$ | H | CH$_3$ | CH$_3$ | CH$_3$ | |
| 2.17 | 2-F | 4-Cl | H | CH$_3$ | CH$_3$ | H | m.p. 85–93° C. |
| 2.18 | H | 4-Cl | H | CH$_3$ | CH$_3$ | H | |
| 2.19a,b | 2-Cl | 4-Cl | H | C$_2$H$_5$ | CH$_3$ | H | $n_D^{50}$ 1.5510 (isomers A + B) |
| 2.19a | 2-Cl | 4-Cl | H | C$_2$H$_5$ | CH$_3$ | H | $n_D^{50}$ 1.5518 (isomer A) |
| 2.19b | 2-Cl | 4-Cl | H | C$_2$H$_5$ | CH$_3$ | H | $n_D^{50}$ 1.5527 (isomer B) |
| 2.20 | 2-Cl | 4-Cl | H | C$_2$H$_5$ | C$_2$H$_5$ | H | $n_D^{50}$ 1.5548 |
| 2.21 | H | 4-NO$_2$ | H | CH$_3$ | CH$_3$ | H | m.p. 118–125° C. |
| 2.22 | H | 4-Cl | H | CH$_3$ | CH$_3$ | H | m.p. 107–110° C. |
| 2.23a,b | 2-CN | 4-Cl | H | C$_2$H$_5$ | CH$_3$ | H | $n_D^{50}$ 1.5537 |
| 2.24a,b | 4-O—Ph—Cl(4) | 2-Cl | H | H | H | C$_2$H$_5$ | oil |
| 2.25a,b | 4-O—Ph—Cl(4) | 2-CH$_3$ | H | H | H | C$_2$H$_5$ | oil |

TABLE 3

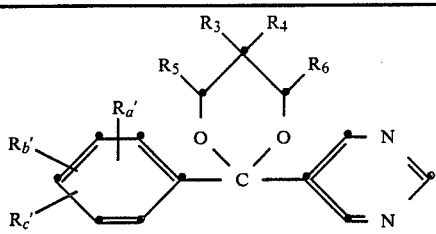

| Comp. | $R_a'$ | $R_b'$ | $R_c'$ | $R_3$ | $R_4$ | $R_5$ | $R_6$ | Physical data |
|---|---|---|---|---|---|---|---|---|
| 3.1 | 2-Cl | 4-Cl | H | H | H | CH$_3$ | CH$_3$ | $n_D^{50}$ 1.5430 |
| 3.2 | 2-Cl | 4-Cl | H | H | CH$_3$ | CH$_3$ | CH$_3$ | $n_D^{50}$ 1.5486 |
| 3.3a | 2-Cl | 4-Cl | H | C$_2$H$_5$ | CH$_2$OH | H | H | $n_D^{50}$ 1.5489 (isomer A) |
| 3.3b | 2-Cl | 4-Cl | H | C$_2$H$_5$ | CH$_2$OH | H | H | m.p. 138–145° C. |
| 3.3a,b | 2-Cl | 4-Cl | H | C$_2$H$_5$ | CH$_2$OH | H | H | |
| 3.4 | 2-Cl | 4-Cl | H | CH$_3$ | CH$_2$OH | H | H | m.p. 154–160° C. |
| 3.5a | 2-Cl | 4-Cl | H | CH$_3$ | CH$_3$ | H | C$_3$H$_7$(i) | m.p. 106–109° C. |
| 3.5b | 2-Cl | 4-Cl | H | CH$_3$ | CH$_3$ | H | C$_3$H$_7$(i) | |
| 3.5a,b | 2-Cl | 4-Cl | H | CH$_3$ | CH$_3$ | H | C$_3$H$_7$(i) | $n_D^{50}$ 1.5438 |
| 3.6a,b | 2-Cl | 4-Cl | H | H | H | H | CH$_3$ | $n_D^{50}$ 1.5476 |
| 3.7a,b | 2-Cl | 4-F | H | H | H | H | CH$_3$ | dark oil |
| 3.8a,b | 2-F | 4-Cl | H | H | H | H | CH$_3$ | $n_D^{50}$ 1.5533 |
| 3.9a,b | 2-CN | 4-Cl | H | H | H | H | CH$_3$ | $n_D^{50}$ 1.5490 |
| 3.10a,b | 2-CN | 4-Cl | H | H | H | H | C$_2$H$_5$ | $n_D^{50}$ 1.5424 |
| 3.11a,b | 2-Cl | 4-Cl | H | H | H | H | C$_2$H$_5$ | $n_D^{50}$ 1.5411 |
| 3.12a,b | 2-F | 4-Cl | H | H | H | H | C$_2$H$_5$ | $n_D^{50}$ 1.5473 |

TABLE O

Compounds of the formula 30

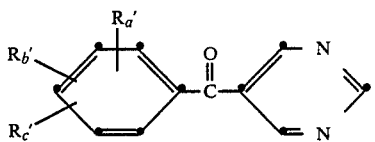

| Comp. | $R_a'$ | $R_b'$ | $R_c'$ | Physical data |
|---|---|---|---|---|
| 0.1 | 2-Cl | 4-Cl | H | m.p. 75–78° C. |
| 0.2 | 2-Cl | 4-F | H | m.p. 64–66° C. |
| 0.3 | 2-Cl | 4-Br | H | m.p. 79–82° C. |
| 0.4 | H | 4-Cl | H | m.p. 127–128° C. |
| 0.5 | H | 4-O—Ph | H | m.p. 120–123° C. |
| 0.6 | H | 4-O—Ph—Cl(4) | H | m.p. 114–116° C. |
| 0.7 | H | 4-O—Ph—Br(4) | H | m.p. 123–126° C. |
| 0.8 | 2-Cl | 4-O—Ph—Br(4) | H | m.p. 112–116° C. |
| 0.9 | 2-F | 4-Cl | H | m.p. 92–96° C. |
| 0.10 | H | 4-NO$_2$ | H | m.p. 122–124° C. |
| 0.11 | 2-Cl | 4-O—Ph—Cl(4) | H | m.p. 108–111° C. |
| 0.12 | 2-OCHF$_2$ | 4-Cl | H | m.p. 65–68° C. |
| 0.13 | 2-OCF$_3$ | 4-Cl | H | m.p. 66–68° C. |
| 0.14 | 2-CN | 4-Cl | H | m.p. 58–61° C. |
| 0.15 | 2-CH$_3$ | 4-O—Ph—Cl(4) | H | m.p. 103–105° C. |
| 0.16 | 2-Cl | 4-Cl | 6-Cl | m.p. 92–96° C. |
| 0.17 | 2-Cl | 4-S—Ph—Cl(4) | H | m.p. 82–87° C. |

2. FORMULATION EXAMPLES FOR LIQUID ACTIVE INGREDIENTS OF FORMULA I (throughout, percentages are by weight)

| 2.1. Emulsifiable concentrates | (a) | (b) | (c) |
|---|---|---|---|
| a compound of Tables 1 to 3 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | (a) | (b) | (c) | (d) |
|---|---|---|---|---|
| a compound of Tables 1 to 3 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | (a) | (b) |
|---|---|---|
| a compound of Tables 1 to 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of Tables 1 to 3 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I (throughout, percentages are by weight)

| 2.5. Wettable powders | (a) | (b) | (c) |
|---|---|---|---|
| a compound of Tables 1 to 3 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Tables 1 to 3 | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of Tables 1 to 3 | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of Tables 1 to 3 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Tables 1 to 3 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Tables 1 to 3 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

Example 3.1.: Action against *Puccinia graminis* on wheat (a) Residual-protective action Wheat plants are treated 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

(b) Systemic action

Wheat plants are treated 5 days after sowing with a spray mixture (0.006% active ingredient, based on the volume of the soil) prepared from a wettable powder formulation of the test compound. After 48 hours the treated plants are infected with a uredospore suspension of the fungus. The plants are then incubated for 48 hours at 95-100% relative humidity and about 20° C. and then stood in a greenhouse at about 22° C. Evaluation or rust pustule development is made 12 days after infection.

Compounds of the Tables exhibit good activity against Puccinia fungi. On the other hand, Puccinia attack is 100% on untreated and infected control plants. After treatment with compounds 1.3a; 1.3b; 1.4a; 1.4a,b; 1.5; 1.7a; 1.7b; 1.7a,b; 1.6a; 1.6b; 1.6a,b; 1.22; 1.24; 1.34; 1.36; 1.37; 1.40; 1.42; 1.44; 1.45; 1.54; 1.58; 2.2; 2.19a,b; 2.20; 2.7; 2.9; 2.12; 2.14; 2.15; 2.23a,b; 2.24a,b; 2.25a,b; 3.6a,b; 3.8a,b; 3.10a,b; 3.11a,b; 3.12a,b, Puccinia attack is 5 to 20% or less.

Example 3.2.: Action against *Cercospora arachidicola* on groundnut plants

Residual protective action

Groundnut plants 10-15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the Tables is substantially reduced. Thus e.g. compounds 1.3a; 1.4b; 1.4a,b; 1.6a; 1.6b; 1.6a,b; 1.34; 1.37; 1.44; 1.45; 1.54; 2.7; 2.9; 2.19a,b; 2.20; 2.23a,b; 3.6a,b; 3.8a,b; 3.11a,b; 3.12a,b inhibit the occurrence of specks almost completely (0 to 10%) in the above test.

Example 3.3.: Action against *Erysiphe graminis* on barley (a) Residual protective action Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

(b) Systemic action

A spray mixture (0.006% active ingredient, based on the volume of the soil) prepared from a wettable powder formulation of the test compound is poured onto barley plants about 8 cm in height. Care is taken that the spray mixture does not come into contact with the parts of the plants above the soil. The treated plants are infected 48 hours later with a conidia suspension of the fungus. The infected barley plants are then stood in a greenhouse at about 22° C. and evaluation of infestation is made after 10 days.

Compounds of the Tables exhibit good activity against Erysiphe fungi. On the other hand, Erysiphe attack is 100% on untreated and infected control plants. Thus e.g. compounds 1.1; 1.3a; 1.3b; 1.3a,b; 1.4a; 1.4a,b; 1.5; 1.6a; 1.6b; 1.6a,b; 1.7a; 1.7b; 1.7a,b; 1.22; 1.24; 1.34; 1.37; 1.40; 1.42,; 1.44; 1.45; 1.54; 1.58; 2.2; 2.7; 2.9; 2.12; 2.14; 2.15; 2.19a,b; 2.19a; 2.23a,b; 2.24a,b; 2.25a,b; 3.6a,b; 3.8a,b; 3.9a,b; 3.10a,b; 3.11a,b; 3.12a,b inhibit fungus attack to 0 to 5%.

Example 3.4.: Residual-protective action against *Venturia inaequalis* on apple shoots Apple cuttings with 10–20 cm long fresh shoots are sprayed with a spray mixture (0.06% active ingredient) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Evaluation of scab infestation is made 15 days after infection. Compounds of the Tables inhibit attack to less than 10%. On the other hand, Venturia attack on untreated and infected shoots is 100%. Thus e.g. compounds 1.3a; 1.34; 1.40; 1.42; 2.19a,b; 2.23a,b; 2.24a,b; 2.25a,b; 3.6a,b; 3.8a,b; 3.9a,b; 3.10a,b; 3.11a,b; 3.12a,b inhibit fungus attack on apple shoots to 0 to 5%.

Example 3.5.: Action against *Botrytis cinerea* on beans

Residual protective action

Bean plants about 10 cm in height are sprayed with a spray mixture (0.02% active ingredient) prepared from a wettable powder formulation of the test compound. After 48 hours the treated plants are infected with a conidia suspension of the fungus. The infected plants are incubated for 3 days at 95–100% relative humidity and 21° C. and then evaluated for fungus attack. Compounds of the Tables inhibit fungus infection very strongly. Thus e.g. compounds 1.3a; 1.3b; 1.3a,b; 1.4a; 1.4b; 1.4a,b; 1.6a; 1.6; 1.6a,b; 1.7a; 1.7b; 1.7a,b and 2.2; 2.12; 2.24a,b; 2.25a,b; 3.6a,b; 3.11a,b reduce fungus attack to 0 to 5%.

Example 3.6.: Action against *Pyricularia oryzae* on rice plants (a) Residual protective action After a cultivation period of 2 weeks, rice plants are sprayed with a spray mixture (0.05% active ingredient) prepared from a wettable powder formulation of the test compound. After 48 hours the treated plants are infected with a conidia suspension of the fungus. Evaluation of fungus attack is made after incubation for 5 days at 95–100% relative humidity and 24° C.

(b) Systemic action

A spray mixture (0.006% active ingredient, based on the volume of the soil) prepared from a wettable powder formulation of the test compound is poured onto two-week-old rice plants growing in earthenware pots customarily used for flowers. The pots are then filled with water until the lowermost stem parts of the rice plants are standing in water. After 48 hours the treated rice plants are infected with a conidia suspension of the fungus. Evaluation of fungus attack is made after incubation of the infected plants for 5 days at 95 to 100% relative humidity and about 24° C.

Compounds of the Tables exhibit good activity against the Pyricularia fungus. On the other hand, Pyricularia attack on untreated and infected control plants is 100%. Thus e.g. compounds 1.3a; 1.3b; 1.4; and 1.6a inhibit fungus attack to 0 to 5%.

EXAMPLE 3.7.: Action against *Rhizoctonia solani* (soil fungus) on rice plants (a) Protective local soil application A spray mixture (0.006% active ingredient) prepared from a formulation of the test compound is poured onto 12-day-old rice plants without contaminating the parts of the plants above the soil. In order to infect the treated plants, a suspension of mycelium and sclerotia of *R. solani* is applied to the surface of the soil. After incubation for 6 days at 27° C. (by day) and 23° C. (by night) and 100% relative humidity (humidity box) in a climatic chamber, fungus attack on the leaf sheath, leaves and stem is evaluated.

(b) Protective local leaf application 12-day-old rice plants are sprayed with a spray mixture prepared from a formulation of the test compound. One day later the treated plants are infected with a suspension of mycelium and sclerotia of *R. solani*. After incubation for 6 days at 27° C. (by day) and 23° C. (by night) and 100% relative humidity (humidity box) in a climatic chamber, fungus attack on the leaf sheath, leaves and stem is evaluated.

Compounds of the Tables exhibit good activity by inhibiting Rhizoctonia attack. On the other hand, attack was 100% on untreated and infected control plants. Thus e.g. compounds 1.3a; 1.3b; 1.4a; 1.4a,b; 1.6a; 1.6b; 1.6a,b; 1.7a; 1.7b; 1.7a,b and 2.2 inhibit fungus attack to 0 to 5%.

What is claimed is:

1. A compound of formula I

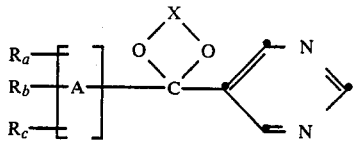 (I)

wherein

A is phenyl, phenoxyphenyl, phenylthiophenyl, biphenyl or naphthyl $R_a$, $R_b$ and $R_c$ are each independently hydrogen, halogen, cyano, nitro, $C_1$-$C_4$alkyl, $C_1$-$C_4$alkoxy, $C_1$-$C_4$haloalkyl or $C_1$-$C_4$haloalkoxy and X is one of the following bridge elements

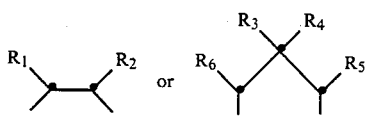

in which formulae $R_1$ and $R_2$ are each independently of the other hydrogen, $C_1$-$C_4$alkyl, $C_1$-$C_4$haloalkyl or $CH_2O$—$C_1$-$C_4$alkyl, $R_4$ is hydrogen, $C_1$-$C_4$alkyl or $CH_2OH$ and $R_3$, $R_5$ and $R_6$ are each independently hydrogen or $C_1$-$C_4$alkyl, or an acid addition salt thereof.

2. A compound of formula I according to claim 1, wherein A, $R_a$, $R_b$, $R_c$, $R_1$ and $R_2$ are as defined above and $R_6$ is hydrogen and $R_3$, $R_4$ and $R_5$ are each independently hydrogen or $C_1$-4alkyl.

3. A compound of formula I according to claim 1, wherein A is phenyl, phenoxyphenyl or phenylthiophenyl, $R_a$, $R_b$ and $R_c$ are each independently hydrogen, halogen, $C_1$-$C_2$alkyl, $C_1$-$C_2$alkoxy, $C_1$-$C_2$haloalkyl, $C_1$-$C_2$haloalkoxy, nitro or cyano, X is one of the bridge elements

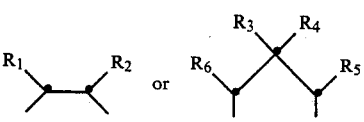

in which formulae $R_1$ and $R_2$ are each independently of the other hydrogen, $C_1$-$C_4$alkyl, $C_1$-$C_2$haloalkyl or $CH_2O$—$C_1$-$C_2$alkyl and $R_4$ is hydrogen, $C_1$-$C_2$alkyl or $CH_2OH$ and $R_3$, $R_5$ and $R_6$ are each independently hydrogen or $C_1$-$C_2$alkyl.

4. A compound of formula I according to claim 2, wherein A is phenyl, phenoxyphenyl or phenylthiophenyl, $R_a$, $R_b$ and $R_c$ are each independently hydrogen, halogen, $C_1$-$C_2$alkyl, $C_1$-$C_2$alkoxy, $C_1$-$C_2$haloalkyl, $C_1$-$C_2$haloalkoxy, nitro or cyano, X is one of the bridge elements

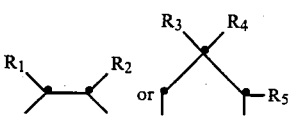

$R_1$ and $R_2$ are each independently hydrogen, $C_1$-$C_4$alkyl, $C_1$-$C_2$haloalkyl or $CH_2O$—$C_1$-$C_2$alkyl and $R_3$, $R_4$ and $R_5$ are each independently hydrogen or $C_1$-$C_2$alkyl.

5. A compound of formula I according to claim 3, wherein A is phenyl or phenoxyphenyl, $R_a$, $R_b$ and $R_c$ are each independently hydrogen, halogen, $C_1$-$C_2$alkyl, $C_1$-$C_2$alkoxy, $C_1$-$C_2$haloalkoxy, nitro or cyano, $R_1$ and $R_2$ are each independently of the other hydrogen, $C_1$-$C_4$alkyl or $CH_2OCH_3$ and $R_4$ is hydrogen, methyl or $CH_2OH$ and $R_3$, $R_5$ and $R_6$ are each independently hydrogen or methyl.

6. A compound of formula I, according to claim 5, wherein A is phenyl or phenoxyphenyl, $R_a$, $R_b$ and $R_c$ are each independently chlorine and/or methyl in the 2- and/or 4-positions and X is the bridge element

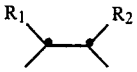

wherein $R_1$ is $C_1$-$C_3$alkyl or $CH_2OCH_3$ and $R_2$ is hydrogen.

7. A compound of formula I according to claim 4, wherein A is phenyl or phenoxyphenyl, $R_a$, $R_b$ and $R_c$ are each independently chlorine or methyl in the 2- and/or 4-positions and X is the bridge element

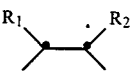

wherein $R_1$ is $C_1$-$C_3$alkyl or $CH_2OCH_3$ and $R_2$ is hydrogen.

8. A compound of formula I according to claim 1, wherein A in combination with $R_a$, $R_b$ and $R_c$ is 2,4-dichlorophenyl, 2-fluoro-4-chlorophenyl, 2-cyano-4-chlorophenyl, 2-methyl-4-chlorophenyl, p-chlorophenoxy, 2-methyl-4-(p-chlorophenoxy) or 2-chloro-4-(p-chlorophenoxy) and $R_1$ to $R_6$ are hydrogen or $C_1$-$C_4$alkyl, $R_1$ to $R_6$ together containing not more than 5 carbon atoms.

9. A diastereoisomer selected from the group consisting of the compounds

5-[2-(2',4'-dichlorophenyl)-4-ethyl-1,3-dioxolan-2-yl]pyrimidine,

5-[2-(2',4'-dichlorophenyl)-4-propyl-1,3-dioxolan-2-yl]pyrimidine,

5-[2-(2',4'-dichlorophenyl)-4-methoxymethyl-1,3-dioxolan-2-yl]pyrimidine,

5-[2-(2',4'-dichlorophenyl)-4,5-dimethyl-1,3-dioxolan-2-yl]pyrimidine,

5-[2-(2',4'-dichlorophenyl)-5,5-dimethyl-1,3-dioxan-2-yl]pyrimidine.

10. A diastereoisomer selected from the group consisting of the compounds

5-[2-(2',4'-dichlorophenyl)-4,6-dimethyl-1,3-dioxan-2-yl]pyrimidine,

5-[2-(2',4'-dichlorophenyl)-4,5,6-trimethyl-1,3-dioxan-2-yl]pyrimidine,

5-[2-(2',4'-dichlorophenyl)-5-ethyl-5-methyl-1,3-dioxan-2yl]pyrimidine,

5-[2-(2',4'-dichlorophenyl)-4-methyl-1,3-dioxan-2yl]-pyrimidine,

5-[2-(2'-cyano-4'-chlorophenyl)-5-etyl-5-methyl-1,3-dioxan-2yl]pyrimidine,

5-[2-(2',4'-dichlorophenyl)-4-ethyl-1,3-dioxan-2yl]-pyrimidine,

5-[2-(2'-chloro-4'-p-chlorophenoxyphenyl)-4-ethyl-1,3-dioxan-2yl]pyrimidine.

11. A fungicidal composition for controlling fungi or for protecting plants from attack by said fungi, which composition contains as at least one active ingredient a compound of formula I accordinag to claim 1 in an amount effective to control said fungi.

12. A method of controlling phytopathogenic fungi or of protecting cultivated plants from attack by said fungi, which method comprises applying to said plants or to the locus thereof a compound of formula I according to claim 1 in an amount effective to control said fungi.

* * * * *